United States Patent [19]
Wientroub et al.

[11] Patent Number: 6,074,833
[45] Date of Patent: Jun. 13, 2000

[54] OSTEOBLAST AND FIBROBLAST ANTIGEN AND ANTIBODIES RECOGNIZING IT

[75] Inventors: Shlomo Wientroub, Tel-Aviv; Dafna Benayahu, Herzlia, both of Israel

[73] Assignee: Ramot University Authority, Ramot-Aviv, Israel

[21] Appl. No.: 08/722,931

[22] Filed: Sep. 30, 1996

[51] Int. Cl.⁷ .............................. G01N 33/53; C12N 5/12; A61K 35/14
[52] U.S. Cl. .................... 435/7.1; 435/326; 435/810; 530/388.1; 530/388.2; 530/388.85; 530/391.1; 530/391.3; 530/391.7
[58] Field of Search ................ 530/388.1, 388.2, 530/388.85, 391.1, 391.3, 391.7; 435/7.1, 810, 326

[56] References Cited

PUBLICATIONS

Burgess et al ( J. Cell Biol., 111: 2129–2138), 1990.
Lazar et al ( Mol. & Cell Biol., 8: 1247–1252), 1988.
Tao et al ( J. Immunol., 143: 2595–2601, 1989.
Shull et al ( PNAS, 86: 5405–5409), 1989.
Isacke et al ( Mol. & Cell Biol., 10: 2606–2618), 1990.
Benayahu et al ( J. Bone & Min. Res. 10: 1496–1503, 1995.
Johnstone & Thorpe ( Immunochemistry in Practice, Blackwell Scientific Pub., Oxford 1987, pp. 49–50).

*Primary Examiner*—Paula K. Hutzell
*Assistant Examiner*—Susan Ungar
*Attorney, Agent, or Firm*—Gary M. Nath; Scott F. Yarnell; Nath & Associates

[57] ABSTRACT

Monoclonal antibodies (MAb) are provided which have binding specificity to an antigen expressed on osteogenic and fibroblastic cells (OFA) and are capable of binding to osteogenic and fibroblastic cells at a substantially higher extent as compared to their binding to skin fibroblasts and stromal adipocytes. Also provided is a novel osteogenic and fibroblastic antigen (OFA) which is expressed on osteogenic and fibroblastic cells at a higher level than its expression in skin fibroblasts and stromal adipocytes having a molecular weight of about 80 kD as determined by western blotting or immunoprecipitation. The OFA and anti-OFA-MAbs are useful in the diagnosis and treatment of various hone related conditions.

7 Claims, 7 Drawing Sheets

OSTEOBLAST AND FIBROBLAST ANTIGEN AND ANTIBODIES RECOGNIZING IT

FIELD OF THE INVENTION

The present invention concerns a novel antigen found in osteoblastic and fibroblastic cells. The present invention also concerns novel monoclonal antibodies which specifically bind to said antigen. The present invention further concerns use of said antigens and antibodies in diagnosis and therapy.

BACKGROUND OF THE INVENTION

Bone is a specialized connective tissue comprising many cell types, extracellular matrix, and minerals. The bone marrow is comprised of stromal and hematopoietic cells.

The stromal compartment of the bone marrow is in itself comprised of a heterogenous cell population including, inter alia, bone-forming cells, known as osteoblasts, which originate from osteoprogenitor cells. Ostcoblasts differentiate into osteocvtcs which are cells surrounded by a mineralized matrix. Very little is known about the mechanisms directing the differentiation of the osteoprogenitors into osteoblasts but it is clear that there is a fine balance between different cellular stages that control the osteoblastic cell renewal and cell loss.

Identification of specific stromal cell types is necessary both for better understanding of the cellular differentiation process in the bone marrow as well as for treatment of various bone diseases. However, to date, specific markers that may be used for recognition and selection of a certain stromal component are very few.

Several antibodies have been developed that recognize cell surface antigens of stromal cells such as the murine IgM monoclonal antibody (MAb) termed STRO-1 which identifies a cell surface antigen expressed by human stromal cells capable of forming CFU-F colonies in vitro (Simmons P. J. et al., STRO-1, *Blood*, 78:55–62 (1991), the MAb termed 6–19 which binds a surface antigenic determinant expressed on several kinds of human cells including bone marrow stromal cells (Iyer, J., et al., *Exp. Hematol*, 18:384–389 (1990) and MAb which binds to a cell surface marker of osteoclasts (Oursler MJO, et al., *J. Cell Biol.* 100:1592–1600 (1985).

Several MAbs obtained by using osteoblastic cells as an antigen have also been reported (Walsh, S., et al., *J. Bone Miner Res.*, 9:1687–1696 (1994) and MAbs which recognize the bone isoenzyme of alkaline phosphatase expressed on the surface of osteoblasts (Tanaka, C., et al., *Cancer Res.*, 46:4853–4857, 1986) were also reported. To date, antibodies that bind specifically to subpopulations of fibroblastic cells are also not available.

Specific markers associated with osteoblasts and fibroblasts that may be used for identifying and selecting osteoblast and fibroblast subpopulations are greatly desired.

Benayahu D. et al., (*Journal of Bone and Mineral Research*, Vol. 10, Number 10, 1995, Blackwell Science, Inc.) describe in their publication which is incorporated herein in its entirety by reference MAb's which recognize an antigen expressed by osteoblasts.

GLOSSARY

Below is a glossary of terms which are used in the following description and claims. However, this glossary should not be considered separately and for full comprehension of the various terms and the meaning in which these terms have in the context of the invention, the glossary should be read in conjunction with the remainder of the disclosure herein.

OFA—osteogenic and fibroblastic cell antigen. An antigen found in osteogenic and fibroblastic cells and not present or only poorly expressed in other types of stromal cells, e.g. strom al adipocytes.

Anti-OFA MAb—a monoclonal antibody which specifically binds and recognizes the OFA.

Binding specificity—the property of an antibody to bind to a certain kind of antigen to a substantially higher extent than its binding to another kind of antigen. In the case of the anti-OFA MAb's, the binding specificity is to OFA.

Cell specific binding—a property of certain antibodies to bind to a substantially higher extent to one type of cell and to a much lesser extent to another type of cell. In the case of the anti-OFA MAb's, the cell binding specificity is to cells expressing OFA, e.g. fibroblastic or osteogenic cells, as compared to a much lower extent of binding to other kinds of cells, e.g. skin fibroblasts and stromal adipocytes.

Binding specificity as well as specific binding are in fact relative measures. In order to determine them, standard methods used for determining binding of antibodies to antigens (e.g. ELISA, radioimmunoassay, FACS analysis etc.) are used to determine the extent of binding of a tested antibody to the antigens or cells of interest. An antibody will be considered to have binding specificity to a certain antigen or cell specific binding to a certain cell when its binding to a tested antigen or cell is substantially higher than its binding to another antigen or cell of comparison. The difference between the binding of an antibody to two antigens or cells of comparison is analyzed statistically (e.g. by Students' T-test) and binding of an antibody will be considered to be "substantially higher" when the difference in its binding of the two antigens or cells is statistically significant.

SUMMARY OF THE INVENTION

The present invention has its basis in novel monoclonal antibodies (MAbs) which were raised initially against marrow osteoblast cells. These MAbs were found to have a cell specific binding to osteoblastic and fibroblastic cells and bound to a very low extent or not at all to skin fibroblasts and marrow adipocytes. The antigen detected by the above MAbs in the cells was termed OFA (osteogenic and fibroblastic antigen) and the MAbs of the invention were termed anti-OFA MAbs. The anti-OFA MAbs can be used for diagnosis and treatment of a variety of diseases associated with alterations in either the number of OFA expressing cells or with alterations in the metabolism of such cells (the change in the metabolic activity of the cells gives rise to a change in the level of expression of the OFA). Furthermore, the monoclonal antibodies can also be used for treatment of diseases associated with such alterations.

The present invention thus provides, by a first of its aspects, an anti-OFA MAb, being selected from a group consisting of:

(a) A MAb having binding specificity to an antigen expressed on osteogenic and fibroblastic cells (OFA), said anti-OFA MAb capable of binding to osteogenic and fibroblastic cells at a substantially higher extent as compared to its binding to skin fibroblasts and stromal adipocytes;

(b) Fragments of the antibodies of (a), which retain the antigen binding properties of the whole MAb; and (c) a conjugated MAb comprising the MAbs of (a) or (b) conjugated to an additional agent.

More specifically, the present invention provides an anti-OFA MAb selected from the group consisting of the MAbs designated herein as MMS-85/12, MMS-25/17, MMS-302/40, MMS-319/4 or fragments of each of the above MAbs retaining the binding properties of the respective whole MAb. In addition, MAbs capable of competitievely interfering with the binding of one of the above anti-OFA MAbs as well as fragments of such a MAb which essentially retain the binding properties of the whole MAb are also within the scope of the invention.

By another of its aspects, the invention provides an OFA protein or polypeptide, being a member of the group consisting of:

(a) an osteoblastic or fibroblastic protein capable of binding to the anti-OFA MAbs of the invention;

(b) analogues of (a) obtained by deletion, addition, replacement or chemical modification of one or more amino acid residues which substantially maintain the binding capability of said analogues to the anti-OFA MAbs of the invention; and (c) fragments of the protein, polypeptides or analogues of (a) or (b) above which essentially retain the binding capacity of the non fragmented polypeptide or protein to the anti-OFA MAbs of the invention.

In addition the present invention provides methods for the diagnosis of bone related conditions as well as methods for treating bone-related conditions using the anti-OFA MAb or OFA of the invention.

Pharmaceutical compositions comprising the anti-OFA MAb or OFA of the invention as well as kits comprising anti-OFA MAbs or OFA together with additional reagents are also all within the scope of the invention.

GENERAL DESCRIPTION OF THE INVENTION

In accordance with the invention, the anti-OFA MAbs can be obtained by immunizing animals, e.g. mammals, mice, rabbits, rats, primates etc., with cells expressing OFA, e.g. with marrow stromal osteoblasts, producing hybridomas by fusing cells from the immunized animals with an immortalized cell line using methods known in the art and selecting for monoclonal producing cell lines. The MAbs are then screened for such MAbs which bind to osteogenic and fibroblastic cells and do not bind or bind to a much lower extent to other fibroblasts, e.g. such as skin fibroblasts or to non-osteoblastic stromal cells such as adipocytes by one of the many methods known in the art.

Typically, where the MAb is intended for treatment in a human, the antigen or cells used for immunizing the animal to produce the anti-OFA MAbs will be of human origin. However, at times there is an inter-species cross reactivity and then it is also possible to use MAbs obtained following immunization with a non-human derived immunogen. Such non-human derived MAbs may also be used, for example, to identify a human OFA within a human cDNA library or human genomic material.

The antibodies may be used as whole antibodies or alternatively fragments of the anti-OFA MAbs having similar binding properties may be used. Such MAb fragments may be, for example, an Fab fragment or an F(ab')$_2$ fragment obtained by cleavage with appropriate enzymes as known in the art. Such fragments will be screened by competitive binding assays with the respective whole anti-OFA MAb and those which are capable of competing with such binding, i.e. bind to the same OFA, may be used. The MAbs in accordance with the invention may belong to any of the various immunoglobulin classes.

The anti-OFA MAbs of the invention can be used for diagnosis or treatment of a variety of diseases and conditions associated with the change in the relative number of osteogenic or fiboblastic cells such as metabolic bone disorders, skelatal dyplasias and bone marrow disorders. In accordance with the invention, the anti-OFA MAbs may be used either in vitro or in vivo.

In accordance with one embodiment of the diagnostic aspect of the invention, the level of OFA in a body sample being a sample of bone marrow, organs, tissues or other body fluids may be determined using the anti-OFA MAbs. Such a sample may be obtained by biopsy or aspiration and reacted in vitro with an anti-OFA MAb preparation. The level of antibodies bound either to the cells or to antigens in the body sample can be assayed, by a variety of means known per se (e.g. ELISA, a variety of radioimmunoassays, FACS analysis, immunohistochemistry etc.).

The anti-OFA MAbs may also be used in vivo, wherein a labeled anti-OFA MAb preparation, (e.g. radioactively labelled) is administered and then the level of the label, e.g. radioactivity, found in the bone or marrow, can be scanned by well known techniques, such as NMR or radionucleide scanning.

In accordance with the therapeutic aspects of the invention, the anti-OFA MAbs may be used in immunotherapy, for example, by binding a variety of cytotoxic agents to the antibodies and administering them to individuals, wherein the number of osteogenic or fibroblastic cells may be controlled in a disease which is associated with an increase in these number of cells, e.g. in various malignancies.

In addition, administration of the anti-OFA MAbs of the invention to an individual may result in neutralization ("blocking") of a portion of the OFA expressed on the osteoblastic and fibroblastic cells. This may be advantageous for the treatment of disorders which are related to over expression of this antigen.

At times, it may be possible to use the anti-OFA MAbs in vitro for therapeutic purposes. For example, cells may be obtained from an individual, incubated in vitro with the monoclonal antibodies conjugated to a cytotoxic agent, and the remaining cells returned to the individual. At other times, it may be possible to use the anti-OFA MAbs to enrich a specific subpopulation of osteoblasts or fibroblasts. This may be desired in various conditions in which there is a decrease in the number of cells of these subpopulations. The enrichment of the cells may be carried out by obtaining a mixed population of cells from an individual, incubating the cells in vitio with the relevant anti-OFA MAb, separating the bound cells (e.g. by sorting them by FACS or by elimination of the non-bound cells), proliferating the purified preparation of cells in vitro and returning the cells to the individual. In addition, there may be conditions under which the incubation of the osteoblasts and fibroblasts with the anti-OFA MAbs may directly induce or inhibit their proliferation and differentiation.

The anti-OFA MAbs may also be used in combination with other modes of treatment. For example, a labelled anti-OFA MAb preparation may be injected into an individual receiving an additional cytotoxic treatment (e.g. chemotherapy administered to a cancer patient) at various periods of time before, during and after the administration of such treatment. The effect of the cytotoxic treatment on the population of cells which binds the labeled MAb may thus be monitored over a desired period of time.

In some cases it may be advantageous to administer the anti-OFA MAbs in combination with other therapeutic agents which can act in an additive or synergistic manner with the MAbs such as various cytokines (e.g. interleukin-1 (IL-1) or interferon-α (IFN-α)).

Specific examples of the anti-OFA MAbs which constitute an additional embodiment of the invention are those termed herein as "MMS-85/12". Other examples are the anti-OFA MAbs termed herein as MMS-25/17, MMS-302/40 and MMS-19/4. The exemplary anti-OFA MAbs, MMS-85/12 (Accession No. 99021801), MMS-25/17 (Accession No. 99021802), MMS-302/40 (Accession No. 99021001) and MMS-319/4 (Accession No. 99021002), were deposited with the European Collection of Cell Culture (ECACC), Vaccine Research and Production Laboratory, Public Health Laboratory Service, Centre for Applied Microbiology and Research, Porton Down, Salisbury, Wiltshire, England.

Furthermore, MAbs capable of competitively interfering with the binding of the above anti-OFA MAbs to OFA constitute an additional embodiment of the invention. "Competitive binding" is to be understood as any binding of a second antibody to OFA or OFA expressing cells which results in a decrease in the binding of a first antibody to the same Ag or cell as determined by standard immunological binding assays and as analyzed by a statistical test.

The MAbs of the invention can also be used to identify, isolate and purify the osteogeenic and fibroblastic antigen—OFA to which they bind. The OFA, which is a novel antigen, constitutes another aspect of the invention.

The OFA was found, in accordance with the invention, to be associated with the cells plasma membrane and also to be secreted by the cells into the extracellar matrix (ECM). The molecular weight of the secreted OFA was found to be about 80 kD as determined by Western blotting and immunoprecipitation.

In accordance with the invention, whole OFA capable of binding to the anti-OFA MAbs of the invention may be used as well as analogues thereof obtained by deletion, addition, replacement or chemical modification of one or more amino acid residues which substantially retain the binding properties to the anti-OFA MAbs of the invention. In addition, fragments of the OFA or of the OFA analogues which essentially retain the binding capacity of the proteins to the anti-OFA MAbs of the invention may also be used.

The OFA of the invention may be obtained by purifying the antigen from cell extracts of an enriched population of OFA expressing cells using any one of the various purification methods known in the art. The OFA of the invention may also be obtained by genetic engineering methods known in the art, e.g. by production of fusion proteins.

By a further embodiment of the invention, the OFA of the invention may also be used for further production of anti-OFA MAbs. For this purpose, the OFA may be used, in vivo, by administering a composition comprising it to an individual in which an immune response will be raised. The OFA may also be incubated, in vitro, with Ab-forming cells under conditions allowing an anti-OFA immune response to occur in the incubated cells.

In accordance with yet another embodiment of the invention, the OFA may also be used for treatment of various conditions in which the level of the OFA is correlated with the condition of an individual in which it is expressed. Thus, for example, administration of a modified OFA to an individual may result in a decrease in the level of non modified OFA in the treated individual.

In addition, as mentioned above with regards to the use of the anti-OFA MAbs, under some circumstances the OFA itself may also be used in vitro for enrichment of a specific desired subpopulation of osteoblastic or fibroblastic cells. This may be especially advantageous in situations in which there is a substantial decrease in the number of cells of the desired subpopulation in an individual due to a disorder or as a side effect of an additional treatment to which the individual was exposed to (e.g. chemotherapy).

The OFA of the invention may furthermore be used for determining the level of anti-OFA MAbs in a sample being bone marrow, organ, tissue or any other body fluids obtained as mentioned above. The OFA is contacted with the sample under conditions enabling its binding to anti-OFA MAbs to form antibody antigen complexes. The formation of the complexes is then detected by any one of the methods known per se using a suitable second antibody.

In accordance with those aspects of the invention wherein the anti-OFA MAbs or OFA are used in vivo, a pharmaceutical composition comprising, as an active ingredient, an effective amount of an anti-OFA MAb or OFA of the invention and a phsyiologically acceptable carrier are administered to a subject in need. Wherein the OFA is administered it may either be in soluble form or bound to a physiologically acceptable carrier. The term "effective atnioitnt" should be understood as meaning an amount of anti-OFA MAb or OFA required to achieve the desired therapeutic effect.

Wherein the anti-OFA MAbs or OFA are administered in vivo to an individual, the administration is typically by means of parenteral administration, e.g. intraveneously, (i.v.), intraperitonealy (i.p.) or intramuscularly. The carrier for administration may be any one of such known per se, e.g. saline solution or any other suitable physiological solution.

A kit comprising either anti-OFA MAbs or comprising OFA together with additional reagents needed for binding of the anti-OFA MAbs to OFA or of the OFA to anti-OFA MAbs respectively and for detection of the formed Ag-Ab complexes also constitutes an aspect of the invention.

The invention will now be illustrated further by the following examples describing experiments demonstrating the binding characteristics of the anti-OFA MAbs of the invention and some characteristics of the OFA with occasional reference to the Figures. It should be noted, however, that this is meant for illustration purposes only and is not to be construed as limiting.

BRIEF DESCRIPTION OF THE FIGURES

FIG. 2 is a photograph showing immunohistochemistry staining by four anti-OFA MAbs to cultured MBA-15 cells, using biotin-avidin peroxidase and DAB as a substrate;

The anti-OFA MAbs were used in three dilutions, 1:100, 1:20 and 1:5.

The Y axis in each of the Figures designates the number of cells showing fluorescence and the X axis shows the fluorescence intensity.

Figure 3A:
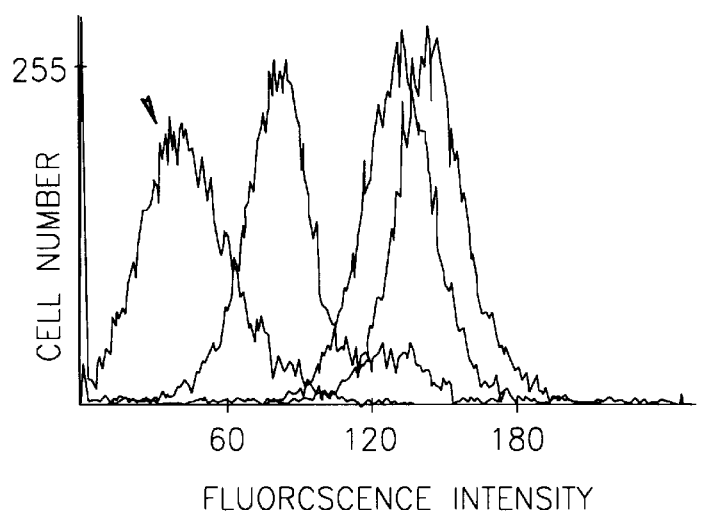
FIG. 3 shows flow cytometry analysis of binding of three different anti-OFA MAbs to MBA-15 cells.
Figure 3B:
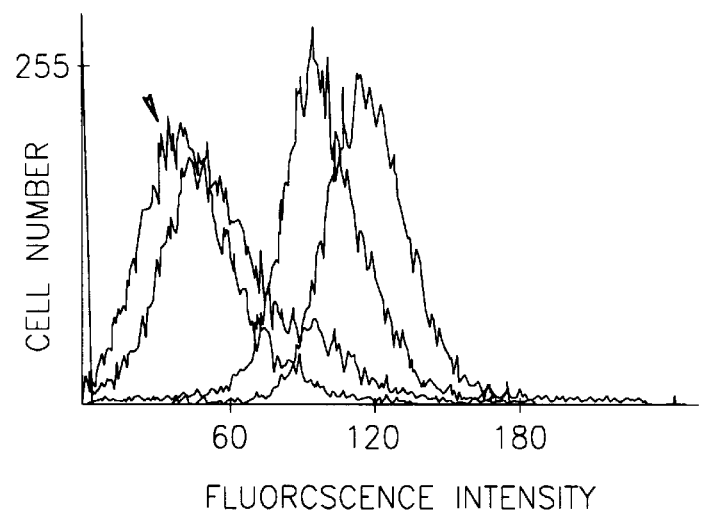
Figure 3C:
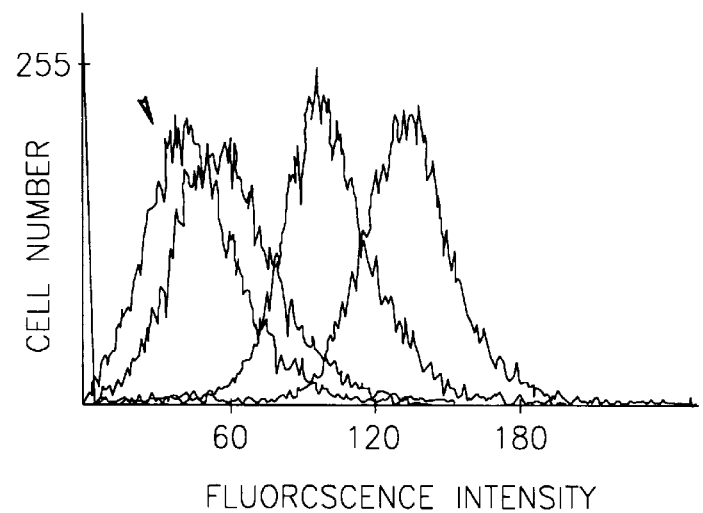

FIG. 3A shows MBA-15 cells stained with different dilutions of MMS-85/12;

FIG. 3B shows MBA-It cells stained with different dilutions of MMS-302/40;

FIG. 3C shows MBA-15 cells stained with different dilutions of MMS-319/4;

The arrow in each of the Figures indicates the fluorescence intensity monitored on MBA-15 cells stained with the second FITC conjugated antibody only.

Figure 4A:
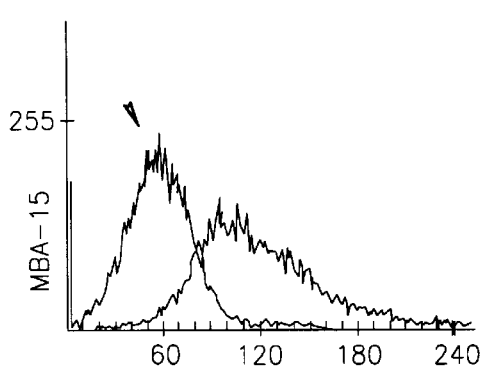
Figure 4B:
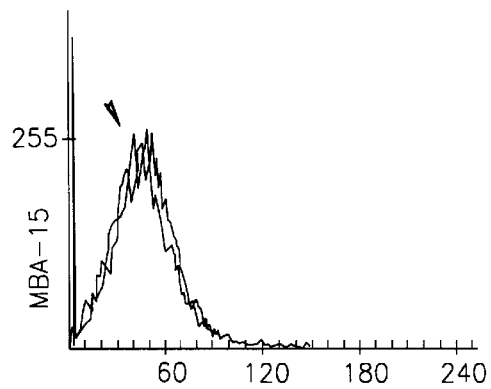
Figure 4C:
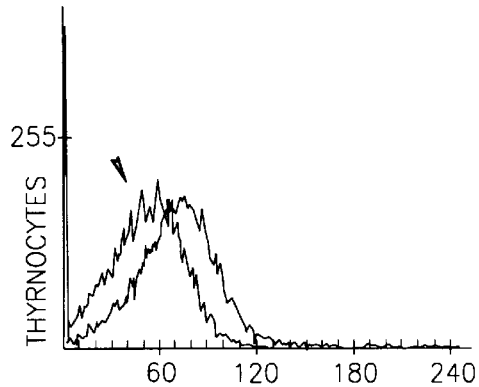
Figure 4D:
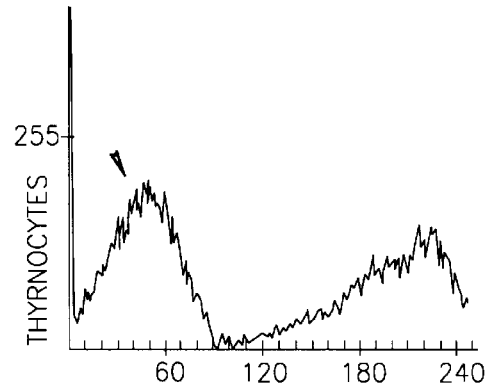
Figure 4E:
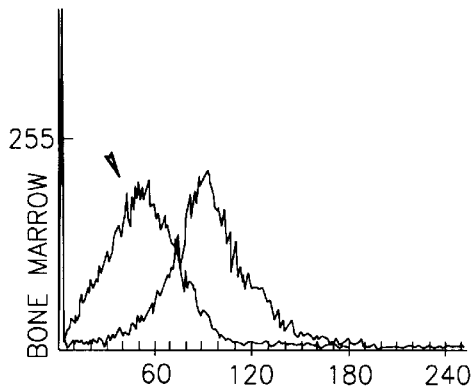
Figure 4F:
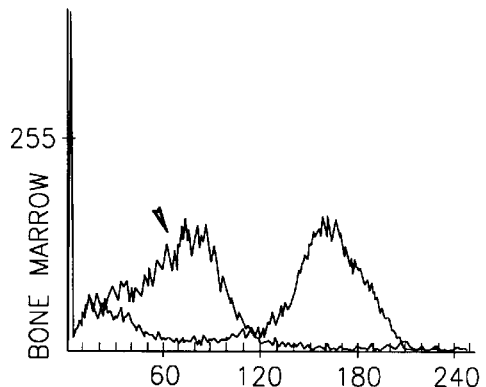

FIG. 4 shows a flow cytometry analysis of MBA-15 cells, thymocytes and bone marrow cells (BMC) double stained with a primary antibody being either the MAb MMS-85/12 anti-θ and αMAC-1 detected with second FITC conjugated antibody. The Y axis shows the number of cells showing a fluoresence intensity and the X axis shows the fluorescence intensity;

FIG. 4A shows MBA-15 stained with MMS-85/12;

FIG. 4B shows MBA-15 stained with anti-θ;

FIG. 4C shows thymocytes stained with MMS-85/12;

FIG. 4D shows thymocytes stained with the anti-θ MAb;

FIG. 4E shows BMC stained with MMS-85/12;

FIG. 4F shows BMC stained with MAC-1 MAb;

The arrow in each of the Figures indicates the fluorescence of cells stained with the second FITC conjugated antibody only.

Figure 5A:
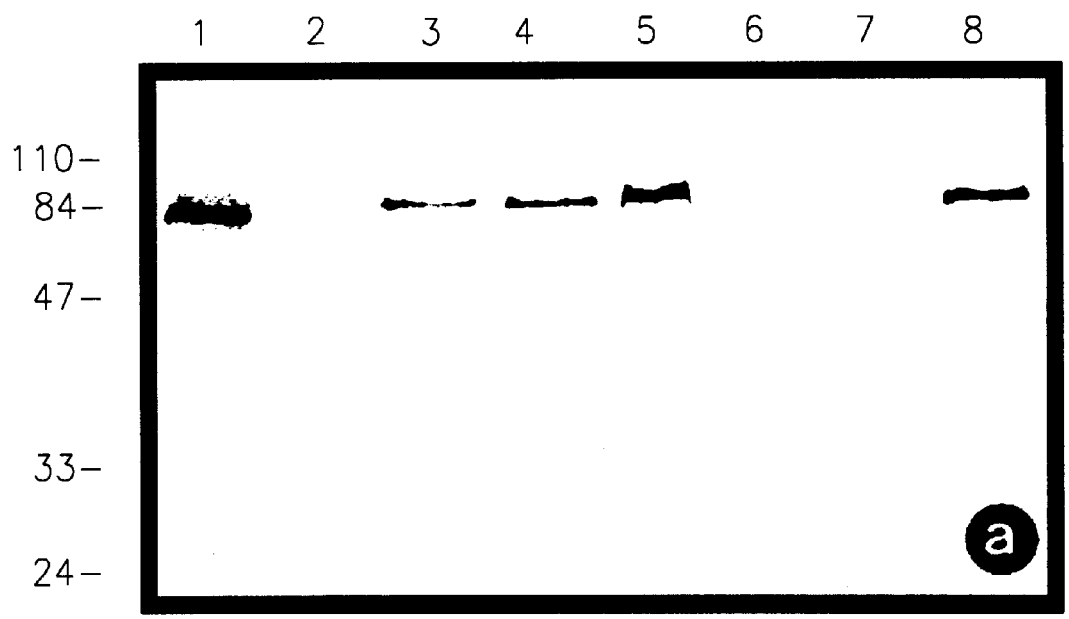

FIG. 5 shows Western blot analysis of the binding of the anti-OFA MAb MMS-85/12 to lysates prepared from various cells;

FIG. 5A lane 1 shows lysates from osteoblastic MC3T3-E1 cells;

FIG. 5A lane 2 shows lysates from osteoblastic cells ROS-17/2.8;

FIG. 5A lane 3 shows lysates from stromal cells subpopulation MBA 1.1.1;

FIG. 5A lane 4 shows lysates from stromal cells subpopulation MBA 13.5;

FIG. 5A lane 5 shows lysates from stromal cell subpopulation MBA 2. 1;

FIG. 5A lane 6 shows lysates of myeloblast cells MI;

FIG. 5A lane 7 shows lysates of adipocytic cells 14F1.1;

FIG. 5A lane 8 shows lysates of osteoblastic cells MBA-15.

Figure 5B:
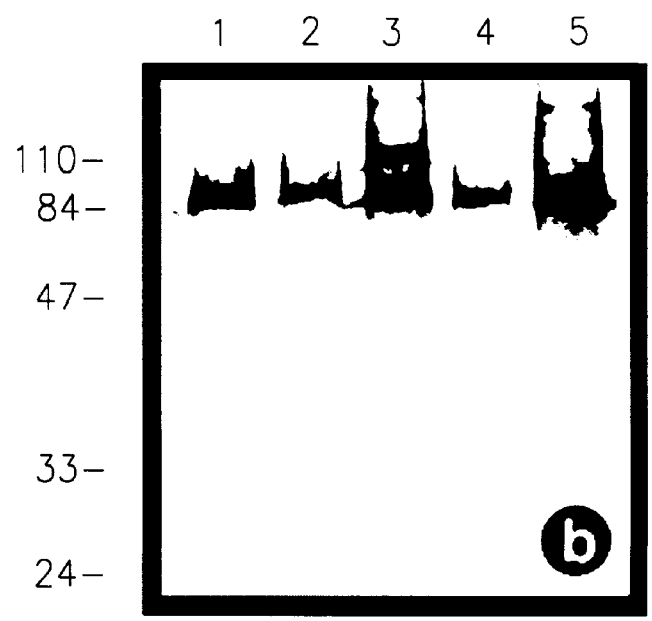
Figure 5C:
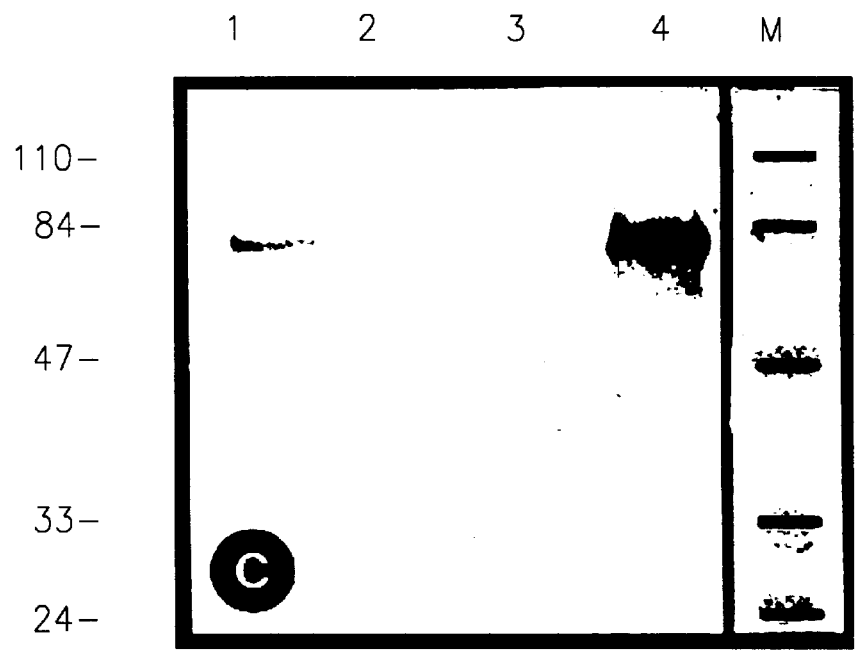

FIG. 5B lane 1 shows lysates from clonal subpopulation of MBA-15 cells;

FIG. 5B lane 2 shows lysates from MBA-15.4 clone;

FIG. 5B lane 3 shows lysates from MBA-15.27 clone;

FIG. 5B lane 4 shows lysates from MBA-15.30 clone;

FIG. 5B lane 5 shows lysates from MBA-15.33 clone;

FIG. 5C shows Western blot analysis of binding of the MMS 85/12 MAb to cells from a primary culture of mouse adherent marrow cells using DAB staining.

Figure 5D:
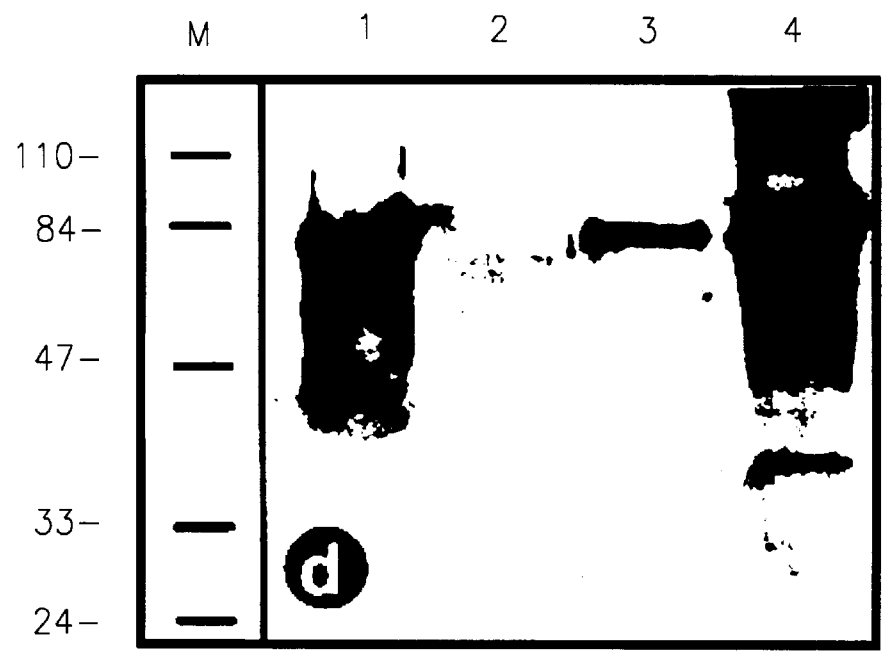

FIG. 5C lane 1 shows lysates of MC-3T3-E1 cells;

FIG. 5C lane 2 shows lysates of 14.F1.1 cells;

FIG. 5C lane 3 shows lysates of primary bone marrow adherent layer cells (BMC);

FIG. 5D shows Western blot analysis of binding of the MMS 85/12 MAb to cells from a primary culture of mouse adherent marrow cells using ECL staining;

FIG. 5D lane 1 shows lysates of MC-3T3-E1 cells;

FIG. 5D lane 2 shows lysates of 14.F1.1 cells;

FIG. 5D lane 3 shows lysates of primary bone marrow adherent layer cells (BMC);

FIG. 5D lane 4 shows lysates of MBA-15 cells.

Figure 6:
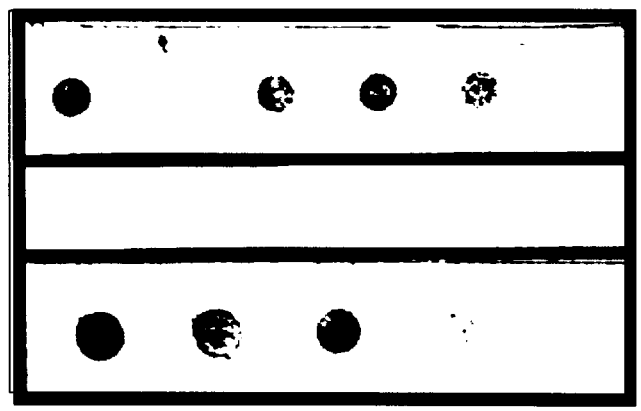

FIG. 6 shows dot blot analysis of conditioned media (CM) harvested from cultures of various stromal cells and osteoblastic cells including clonal sub populations of MBA-15 cells (see FIG. 5 above) with the anti-OFA MAb MMS-85/12;

FIG. 6 lane 1 shows CM harvested from MBA 2.1 cells;

FIG. 6 lane 2 shows CM harvested from ROS 17/2.8 cells;

FIG. 6 lane 3 shows CM harvested from MBA-1.1.1 cells;

FIG. 6 lane 4 shows CM harvested from MBA-13.5 cells;

FIG. 6 lane 5 shows CM harvested from MBA-15 cells;

FIG. 6 lane 6 shows CM harvested from MBA-15.4 cells;

FIG. 6 lane 7 shows CM harvested from MBA-15.6 cells;

FIG. 6 lane 8 shows CM harvested from MBA-15.33 cells;

FIG. 6 lane 9 shows CM harvested from MC3T3-E1 cells;

FIG. 6 lane 10 shows CM harvested from 14 F 1.1 cells.

Figure 7:
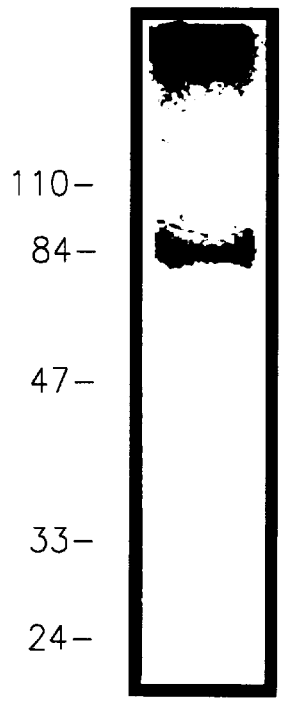

FIG. 7 shows an autoradiogram prepared by immunoprecipitation of a cell lysate prepared from [$^{35}$S]-methionine radio-labeled MBA-15 cells using the anti-OFA MMS-85/12 MAb.

DETAILED DESCRIPTION OF THE INVENTION

Materials and Methods a) Cells

Osteogenic marrow stromal MBA cells derived from SJL/J mice (Benayahu D, Kletter Y, Zipori D, Wicntroub S, 1989, "Bone marrow-derived stromal cell line expressing osteoblastic phenotype in vitro and osteogenic capacity in-vivo", *J. Cell Physiol.*, 140:1–7) and clonal subpopulations (Fried A, Benayahu D, Wientroub S, 1993, "Characterization of clonal subpopulations of marrow-derived osteogenic cells (MBA-15): putative stages in osteoblast differentiation," *J. Cell Physiol.* 155:472–482) were seeded in tissue culture dishes (Nunc, Denmark) in Dulbecco's modified Eagle's medium (DMEM, Beth Haemek, Israel) containing high glucose supplemented with 10% fetal calf serum (FCS, Bio-Lab, Israel). Stocks of cells were passaged once wcckly by removal with a rubber policeman and dispersed in fresh medium. All cultures were incubated at 37° C. in a humidified atmosphere of 10% $CO_2$ in air. Other stromal cells used were MBA-1.1.1, MBA-2.1, MBA-13.5, and 14F1.1. (Benayahu D, Fried A, Zipori D, Wicntroub S, 1991, "Subpopulations of marrow stromal cells share a variety of osteoblastic markers", *Calcif Tissue Int.* 49:202–207). The osteoblastic cells of nonstromal origin included in this study were MC3T3-E1 and ROS 17/2.8, cell lines and primary cultures of calvaria cells and adherent marrow cells. Other nonosteoblastic cell types, such as myeloblasts (Ml), kidney epithelia (Cos), and neuroblastoma (IMS), were grown under the same conditions. Macrophages (14Ml) were grown with the addition of L cell-conditioned medium as a source for CSF-1.

b) Immunization and hybridization

BALB/c mice were immunized with $5\times10^6$ MBA-15 cells per mouse by subcutaneous (SC) injection in complete Freund's adjuvant. The initial injection was followed two weeks later by an SC injeciton using incomplete adjuvant followed by another three intraperitoneal (ip) injections every two weeks. Ten days later, the sera were tested for the immune response to cultured cells, using colorimetric enzyme-linked immunosorbant assay (ELISA). The animal that showed a high titer received another intravenous (iv) or ip injection with $5\times10^6$ cells three days prior to splenocyte fusion. Splenocytes were fused with NSO myeloma cells using polyethylene glycol 4000 (Merck, Germany) as the fusing agent. The fusion product was plated into 96-well plates in hypoxanthine-aminopterin-thymidine (HAT) medium supplemented with 10% FCS according to the method of Kohler and Milstein, (Kohler G, Milstein G, 1975, "Continuous cultures of fused cells secreting antibody of predefined specificity", Nature, 256:495–497) at the Hybridoma Unit of the Faculty of Life Sciences, Tel-Aviv University.

c) IgG subclass determination

The isotyping for monoclonal antibodies was determined using the Scrotec Kit (Wellcome Ltd., U.K.), employing test based on red cell agglutination.

d) Screening assay for selection of MAb by ELISA

The specific antigen determination of secreting hybridomas was identified on cultured cells. Examined cells were plated for 4 days in 96-well plates, after which the plates were washed with phopsphate-buffered saline (PBS) and fixed in 0.3% paraformaldchyde in PBS. For the assay itself, the cells fixed in the plates were blocked with skim milk and incubated with the respective primary antibodies overnight. A second antibody peroxidase-conijugated goat anti-mouse immunoglobulin (BioRad Lab. Ltd., Herts, U.K.) (1:3000) was added for 30 minutes and incubated at 4° C. After rinsing, the cultures were incubated at 37° C. with substrate solution containing 2 mg/ml O-phenylenediamine (OPD) (Sigma Chemical Co., St. Louis, Mo.) in 50 mM citric buffer pH 5.0 and 30 $\mu$ 30% $H_2P_2$. The reaction was stopped after 15 minutes by the addition of 4 N HCl. Optical density (OD) was read on a microplate reader system at 490–405 nm (Molecular Devices, Palo Alto, Calif.).

e) Flow cytometric analysis

MBA-15 cells were released from culture with trypsin and prepared as single cell suspensions. Mouse bone marrow cells (BMC) and thymocytes were freshly isolated from mice. A total of $1\times10^5$ cells were fixed in 0.3% paraformaldehyde in PBS and rinsed in 0.2% Triton X-100 (Sigma Chemical Co.) in PBS. Following incubation with the first antibody for 90 minutes on ice with occasional agitation, they were rinsed in PBS and incubated with goat anti-mouse FITC-conjugated secondary antibody (Zymed Lab, San Francisco, Calif.) for 30 minutes. Cells were washed in PBS and $1\times10^4$ cells were collected for each sample. The accuracy of positive cells fluorescently labeled with various MAbs was quantified with four-parameter fluorescence-activated cell sorter (FACS) (Beckton-Dickinson).

f) Gel electrophoresis and Western blotting analysis

The harvested cultured cells were washed twice with PBS, and the pellets of cells were frozen at −20° C. Various organs were removed from the animal, homogenized in TENN buffer (50 mM Tris, 5 mM EDTA, 0.5% NP40, 150 mM NaCl, pH 7.4 with 1 mM phenylmethyl-sulfonylfluoride (PMSF) using a Polytron homogenizer (Kinematica, Switzerland) on ice. The extracts were centrifuged for 15 minuts at 7000 g and at a temperature of 4° C. Demineralized long bones were extracted by EDTA (E extracts) and other purified proteins such as osteonectin (ON), bone sialoprotein (BSP) and alkaline phosphatase (ALK-P) were prepared from demineralized bone matrix of various species as described earlier by Fisher et al. (Fisher L. W, Hawkins G. R, Tuross N, termine J. D, 1987, "Purification and partial characterization of proteoglycans I and II, bone sialoproteins I and II, and osteonectin from the mineral compartment of developing human bone", J. Biol. Chem., 262:9702–9708. All samples were prepared for extraction in sodium dodecyl sulfate (SDS), boiled for 3 minuts and dissolved in a sampling buffer (62.5 mM Tris-HCl, pH 6.8,2% SDS, β-mercapto-ethanol, and 0.01% bromophenol blue). Two to 5 $\mu$g of protein from the samples were used for electrophoresis separation in a 0.75 mm-thick mini-gel of 10% SDS-PAGE polyacrylamide slabs gels with a 2.5% polyacrylamide stacking gel. A horizontal electrophoresis apparatus (BioRad Lab. Ltd.) was used to separate the proteins (Laemmli, U.K.,1970 "cleavage of structural proteins during the asembly of the head of bacteriophage T4", Nature, 227:680–685. The proteins were then clectroblotted to a nitrocellulose membrane using a semi-dry transfer blotting apparatus (BioRad Lab., Ltd), by a modification of Hurley and Frinkelstein's method (Hurley W. L., Frinkelstein E, 1985 "Identification of surface proteins on bovine leukocytes by a biotin-avidin protein blotting technique", J. Immunol, Meth. 85:195–202. Nitrocellulose blots were blocked in skim milk and incubated first with MAb for 30 minutes at 37° C. or overnight at 4° C. and then with peroxidase-conjugated affinity purified antibody to mouse IgG (Biorad Lab, Ltd.). The blots were exposed to a freshly prepared solution containing either diaminobenzidine tetrahydrochloride (DAB) (Sigma Chemical Co.) or ECL (Amersham, U.K.). The latter substrate is used for providing higher sensitivity for visualization of the Ag-Ab complex on the blot.

g) Metabolic labeling and immunoprecipitation of antigens

New antigens synthesis was detected by incuabation of $3\times10^5$ cells in mcthionine-free medium supplemented with 125 $\mu$Ci L-[$^{35}$S] methionine (Du Pont, NEN, U.K.) at 37° C. for 4 hours. Following labeling, the cells were lysed according to the method of Jeffries et al. (Jeffries W. A., Ruther E. F., Kvist S, 1988 "Cytolitic T cells recognize a chimeric MHC class 1 antigen expressed in influenza A-infected transgenic mice", EMBO J.,7:3423 modified with an addition of 0.5% (v/v) NP40,150 mM EDTA, 5 Mm iodoacetamide, 2 mM L-methionine, 0.5% (w/v) BSA, 150 Mm nAcL, and 1 mM PMSF in Tris-HCL, Ph 6.8. Nuclei were removed by centrifugation at 7000 g for 5 minutes. A 10% (v/v) suspension (0.1 ml) of protein A-sepharose CL-4B (Pharmacia, Sweden) previously saturated with rabbit anti-mouse IgG was prepared. Hybridoma supernatant was added to aliquots of the mixture of cell lysate and protein A. Immunoprecipitates were released from the beads by boiling them in a sample buffer and then analyzed by SDS-PAGE (Laemmi UK 1970, "Cleavage of structural proteins during the assembly of the head of bacteriophage T4" Nature, 227: 680–685) followed by fluorography (Laskey R. A., Mills A. D., 1975 "Quantitative film detection of $^3$H and $^{14}$C in polyacrylamide gels by fluorography", Eur. J. Biochem, 56:335–341).

h) Dot blot of conditioned media

Conditioned media (CM) from varioius stromal cell lines were harvested from confluent cultures. Each medium was removed from cultured cells and replaced by fresh growth medium containing 2% FCS in DMEM free of phenol red. The CM were collected after 48 h,millipore (0.45 $\mu$m)-filtered, and examined for their antigen expression.

i) Immunocytochemistry of cultured cells

Cells were cultured on glass coverslips fixed for 10 minutes at −20° C. in methanol and acetone, washed, and then incubated for 30 minutes in 0.01% $H_2O_2$ to deplete any endogenous peroxidase activity. After washing, the cells were preincubated for 20 minutes in skim milk. The coverslips were incubated overnight at 4° C. with the hybridoma culture supernatant washed twice for 5 minutes each time and incubated for 30 minuts with affinity-purified biotin-labeled rabbit anti-mouse (Bio-Makor, Israel) diluted at 1:100, followed by avidine-peroxidase (Bio-Makor, Israel). The cells were then exposed to 0.1% DAB (Sigma Chemical Co.) used as a substrate and then counterstained with hematoxylin.

EXAMPLES

Example 1
Production of anti-OFA MAbs 330 hybridomas were produced by immunization of mice with MBA-15 osteogenic marrow stromal cells and stenoisides of the injected mice were fused to produce hybridomas as described in Material and Methods (a) and (b) above. 330 hybridomas were produced in two fusion experiments and from these, four MAbs of interest were selected and termed MMS- 85/12, MMS-25/17, MMS-319/4 and 302/40 by their binding affinity to various culture cells, as determined in an ELISA assay (see Materials and Methods (b) above). The above MAbs will hereinafter be referred to at times by using their designated number alone (e.g. 85/12). The binding affinity of each of the four selected MAbs to cultured MBA-15 cells was compared to their binding to two other cultured osteoblastic cell lines, ROS-17/2.8 and MC3T3-E$_1$ as well as to cultured skin fibroblasts originating from the same mouse strain as the above mentioned osteoblastic cell cultures (SJL).

Figure 1:
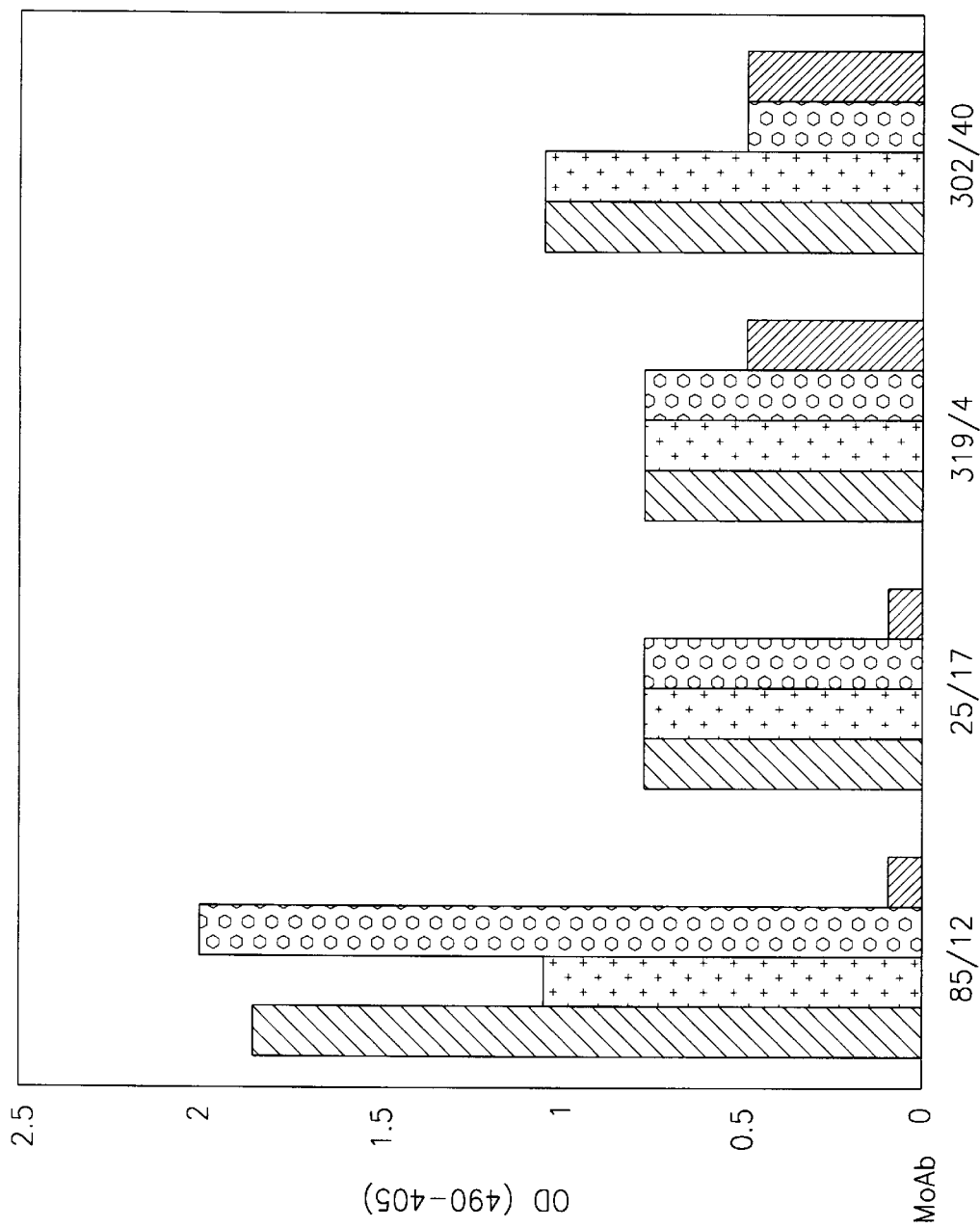
FIG. 1 is a graphical presentation of results of an experiment showing binding of four anti-OFA MAbs to four different kinds of cells as measured by ELISA immunoassay.

As seen in FIG. 1, each of the four tested MAbs were capable of binding to antigens on each of the four kinds of cultured cells. The binding affinity of each of the four MAbs to each of the tested cells was different. MMS-85/12 and MMS-25/17 had a higher binding affinity to the three osteoblastic cell cultures, as compared to their binding affinity to the mouse-derived skin fibroblast to which they bound at a very low extent.

MMS-319/4 and MMS-302/40 bound the skin fibroblasts at a higher affinity than the above two MAbs, but they too bound the osteogenic cell cultures at an at least equal or higher affinity than their affinity to the skin fibroblasts.

The isotype and subclass of each of the above anti-OFA MAbs was determined (see Materials and Methods (c) above). MMS-85/12 and MMS-25/17 were identified as IgG-1, MMS-319/4 were found to be IgG-3 and MMS-302/40 were determined to be an IgM antibody.

Example 2
Cellular localization of OFA

In order to determine the cellular localization of the antigens in the MBA-15 cells to which each of the above four anti-OFA MAbs was capable of binding to, an immunohistochemistry staining assay was carried out as described in Materials and Methods (i) above.

Figure 2A:
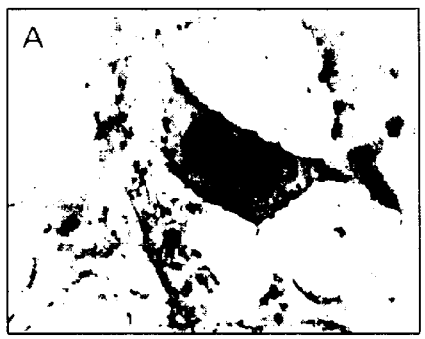
FIGS. 2A and 2B show staining by the MAb MMS-85/12.
Figure 2B:
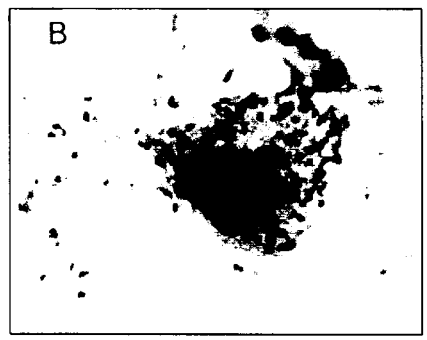
Figure 2C:
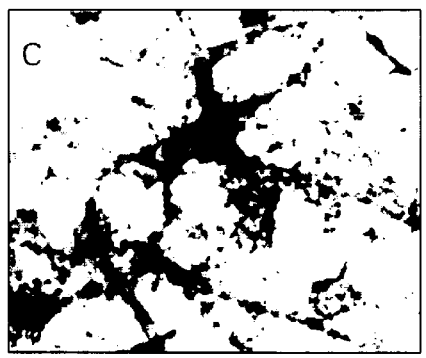
FIGS. 2C and 2D show staining by the MAb MMS-25/17.
Figure 2D:
Figure 2E:
FIG. 2E shows staining by the MAb MMS-302/40.
Figure 2F:
FIG. 2F shows staining by the MAb MMS-319/4.

As seen in FIG. 2, and as summarized in Table 1 below, the anti-OFA MAb MMS-85/12 stained a cell membrane associated with molecules present at the cell surface of the cells and in the ECM components deposited between the cells (FIGS. 2A and 2B), anti-OFA MAb 25/17 and molecules present in the ECM (FIG. C and D) and anti-OFA MAbs 302/40 and 319/4 bound to intracellular cytoplasmic components (FIGS. 2E and 2F, respectively). Similar results were also obtained in an immunohistochemistry assay using primary calvaria cells and MC3T3-E1 cells (data not shown).

TABLE 1

Immunohistochemistry of Cultured Cells with MMS MAbs

| Localization | 85/12 | 25/17 | 302/40 | 319/4 |
|---|---|---|---|---|
| Extracellular matrix (ECM) | + | + | − | − |
| Cell surface | + | + | − | − |
| Cytoplasmatic | − | − | + | + |

Example 3
OFA expressed in sillglc cell suspensions of MBA-15 cells

Single cell suspenions were prepared from MBA-15 cell cultures. The cells were stained and analyzed by flow cytometry as explained in Materials and Methods (e) above.

As can be seen in FIG. 3, the three anti-OFA MAbs MMS-85/12 (FIG. 3A), MMS-3()2/40 (FIG. 3B) and MMS-319/4 (FIG. 3C) stained the MBA-15 cells. The fluorescence intensity of the assorted cells was in direct correlation to the dilution of the antibody used for staining.

Example 4
Distribution of OFA and its MW:

The nature of the antigen recognized by the various anti-OFA MAbs in various stromal cells was determined by preparing lysates from the various tested cells, separating them by SDS-PAGE gel, electroblotting the separated lysates onto a nitrocellulose membrane and reacting them with the various tested anti-OFA MAbs, as described in Materials and Methods (f) above.

(a) The antigens recognised by the three anti-OFA MAbs MMS-85/12, MMS-302/40 and MMS-25/17 were determined in several types of stromal cells. As seen in Table 2 below, MMS-85/12 and MMS-302/40 detected in the cells bands with a molecular weight of 84 kD and 75 kD, respectively. The antigens recognized by the above two anti-OFA MAbs had a similar distribution on MBA-1, MBA-13.5, MBA-1.1.1 and MBA-2.1 stromal cells. The anti-OFA MAb MMS-85/12 did not bind to any antigenic epitope on the 14F1.1 adipose cell lysate. The anti-OFA MAb MMS-25/17 bound two bands in all the stromal cell lysates, as well as an additional third band at a lower weight of 35 kD, which was expressed only in the MBA-15 cell lysate.

TABLE 2

Western Blotting Analysis of Various Marrow Stromal Cell Types and Osteoblastic Cells with Specific MAbs

| MMS | No. of bands | Approx. MW of Ag | Stromal Cell lines | | | | |
|---|---|---|---|---|---|---|---|
| | | | MBA 15 | MBA 13.5 | MBA 1.1.1. | MBA 2.1 | 14F-1.1 |
| 85/12 | 1 | 84 | + | + | + | + | − |
| 302/40 | 1 | 75 | + | + | + | + | ND |
| 25/17 | 2 or 3 | 30–40 | +++ | ++ | ++ | ++ | ND |

(b) Bone-E extracts were prepared from various animal species as described in Methods and Materials (f) above and were then incubated with the various anti-OFA MAbs. The anti-OFA MAb MMS-85/12 bound an antigen in mouse E-extract having an apparent MW similar to that detected in the cell lysates (i.e. about 80 KD). A low extent of binding of the same MAb was detected in rat E extracts. The purified proteins, osteonectin (ON) and bone sialoprotein (BSP) which were prepared from the E extracts were not bound by any of the tested anti-OFA MMS MAbs.

(c) Various tissue extracts originating from mice were also separated by SDS-PAGE gel electroblotting onto cellulose membrane and incubated with two anti-OFA MAbs MMS-85/12 and MMS-25/17.

As seen in Table 3 below, the two tested anti-OFA MAbs did not bind any of the tissue extracts except for total bone marrow which was bound by the MMS-85/12 MAb. As described below, (see Example 6 and FIGS. 5C and 5D), the cells in the bone marrow which bound the MMS-85/12 MAb were apparently marrow stromal cells which are present at a relatively low frequency within the whole bone marrow.

TABLE 3

Western Blotting Analysis of MBA-15 Cells Compared With Mouse Tissue Extracts Examined by MAbs MMS-85/12 and MMS-25/17

| Tissue | MMS-85/12 | MMS-25/17 | Desmin |
|---|---|---|---|
| MBA-15 | + | + | − |
| Spleen | − | − | + |
| Total bone marrow | + | − | + |
| Thymus | − | − | = |
| Liver | − | − | ± |
| Lung | − | − | + |
| Heart | − | − | + |
| Muscle | − | − | + |
| Kidney | − | − | ± |

MAb anti-Desmin was used as a positive control in this assay. Lysates from cells expressing various antigens were separated by the SDS-PAGE gel and by electroblotting them to a nitrocellulose membrane. The Ab-Ag complex was visualized by DAB used as a substrate.

Example 5
Binding specificity of the anti-OFA MMS-85/12—FACS analysis:

Single cell suspensions of freshly isolated thyomcytes and bone marrow cells (BMC) were prepared, stained and analyzed by FACS as described in materials and Methods (e) above, using the anti-OFA MAb MMS-85/12 as a first antibody.

As seen in FIG. 4, the fluorescence intensity on the thymocytes stained by the MMS-85/12 were similar to the fluorescence intensity on the same cells stained only with the second antibody, thus indicating no binding of this anti-OFA MAb to the thymocytes. The fluorescence intensity of the BMC stained with the MMS-85/12 MAb was low but significantly higher than the fluorescence intensity detected on the same cells, stained with only the second antibody. Thus, the MMS-85/12 anti-OFA MAb recognized an antigen expressed in bone marrow cells but did not recognize any antigens expressed in thymocytes.

Example 6
Characterization of the identified by the anti-OFA MMS-85/12:

Lysates from various cells were separated on SDS PAGE gel and then subjected to Western blotting analysis as described in Materials and Methods (f) above.

As seen in FIG. 5A, a band having a molecular weight of 84 kD was detected in lysates of osteoblastic MC3T3-E1 (lane 1), of several clones of stromal cells (lanes 3–5) and in a lysate from MBA-15 osteoblastic cells (lane 8).

As seen in FIG. 5B, the same 84 kD band was detected in lysates of several MBA-15 clonal cell lines which each represents a different stage of differentiation along the osteoblastic lineage.

As seen in Table 4 below, Western blot analysis of lysates from various other kinds of cells with the MMS-85/12 MAb did not detect an antigen in any of these cell types, except for in primary adherent bone marrow stromal cells.

As can be seen in FIGS. 5C and D, the 84 kD antigen was detected in lysates of enriched primary cultured mouse adherent marrow cells subjected to Western blot analysis using either DAB (FIG. 5C) or ECL (FIG. 5D) as a substrate. These cells apparently account for the positive binding of MMS-85/12 to BM extract (see example 4 above).

TABLE 4

Western Blotting Analysis of Specific Cell Lines Examined by MMS-85/12

| Nonosteoblastic cells | MMS-85/12 |
|---|---|
| T-Lymphocyte | − |
| Myeloblast (M1) | − |
| B-Lymphocyte | − |
| Macrophage (14M1) | − |
| Kidney epithelial (cos+) | − |
| Neuroblastoma (IMS) | − |
| Primary adherent bone-marrow stroma | + |

Lysates from cells expressing various antigens were separated by an SDS-PAGE gel and electroblotting them to a nitrocellulose membrane. The Ab-Ag complex was visualized by DAB or ECL used as a substrate.

Example 7
Binding of the MMS-85/12 MAb to conditioned media (CM)

CM was prepared from cultures of various stromal and osteoblastic cells and subjected to dot blot analysis as described in Materials and Methods (h) above. As seen in FIG. 6, the results of this experiment positively correlated to the results described in Example 4 above. The MMS-85/12 MAb bound to CM of each of the cell cultures in which the OFA was detected (by western blotting). These results demonstrate that the antigen recognized by the MMS-85/12 in osteoblastic cells is also secreted from the cells to the culture medium.

Example 8
Characterization of the antigen detected by the MMS-85/11 MAb—immunoprecipitation:

In order to verify that the antigen recognized by the anti-OFA MAb MMS-85/12 in the osteoblastic cells is indeed the 84 kD antigen, MBA-15 osteoblastic cells were metabolically labeled and subjected to immunoprecipitation as described in Materials and Methods (g) above.

As seen in FIG. 7, an 84 kD protein was immunoprecipitated from the MBA-15 cells by the MMS-85/12 MAb, similarly to the protein detected in the MBA-15 cell lysate using Western blotting techniques (see Example 6 above).

Example 9
Cross reactivity of the Ag recognized by MMS-85/12 MAb with the bone alkaline phosphatasc protein (ALK-P):

The ALK-P is a bone isoenzyme of alkaline phosphatase which is highly expressed on the surface of osteoblasts and has a molecular weight of 80 kD (Tanaka et al., Supra). In order to rule out the possibility that the MMS-85/12 MAb recognized the ALK-P antigen in the osteoblast cells, its capability to bind purified ALK-P was tested by a western blotting analysis as described above. The results of this experiment showed that the MMS-85/12 MAb clid not bind to the ALK-P purified protein.

We claim:

1. A monoclonal antibody (Mab) that binds to the same epitopes as a MAb being selected from the group consisting of:

(a) a MAb designated as MMS-85/12 (Accession No. 99021801), MMS-25/17 (Accession No. 99021802), MMS-302/40 (Accession No. 99021001) or MMS-319/4 (Accession No. 99021002) having binding specificity to an antigen expressed on osteogenic and fibroblastic cells (OFA) which is increased over its binding specificity to skin fibroblasts and stromal adipocytes; and (b) a conjugated MAb comprising the MAbs of (a) conjugated to an enzymatic agent, a radioactive agent or a cytotoxic agent, said conjugated MAbs retaining the binding characteristics of the nonconjugated MAb; wherein said antigen has a molecular weight of about 80 kD as determined by Western blotting or immunoprecipitation and is localized in the cell plasma membrane and extracellular matrix.

2. A MAb capable of competitively interfering with the binding of one of the anti-OFA MAbs designated as MMS-85/12 (Accession No. 99021801), MMS-25/17 (Accession No. 99021802), MMS-302/40 (Accession No. 99021001) or MMS-319/4 (Accession No. 99021002) to OFA or an antigen binding fragment thereof; wherein said OFA has a molecular weight of about 80 kD as determined by Western blotting or immunoprecipitation and is localized in the cell plasma membrane and extracellular matrix.

3. An anti-OFA MAb being an MAb designated as MMS-85/12 (Accession No. 99021801), MMS-25/17 (Accession No. 99021802), MMS-302/40 (Accession No. 99021001) or MMS-319/4 (Accession No. 99021002) having binding specificity to an antigen expressed on osteogenic and fibroblastic cells (OFA) or antigen binding fragments of each of the above MAbs; wherein said OFA has a mlecular weight pf about 80 kD as determined by Western blotting or immunoprecipitation and is localized in the cell plasma membrane and extracellular matrix.

4. A composition comprising a MAb according to claim 1, together with a pharmaceutically acceptable carrier.

5. A kit comprising a MAb according to claim 1, together with reagents necessary for detection of Antibody-Antigen complexes in a tested sample.

6. A hybridoma which produces a monoclonal antibody designated as MMS-85/12 (Accession No. 99021801), MMS-25/17 (Accession No. 99021802), MMS-302/40 (Accession No. 99021001) or MMS-319/4 (Accession No. 99021002) that preferentially binds to a osteogenic or fibroblastic cell surface antigen; wherein said antigen has a molecular weight of about 80 kD as determined by Western blotting or immunoprecipitation and is localized in the cell plasma membrane and extracellular matrix.

7. A method for the detection of an antigen expressed on osteogenic and fibroblastic cells (OFA), which comprises:

a MAb according to claim 1, together with reagents necessary for detection of Antibody-Antigen complexes in a tested sample.

* * * * *

UNITED STATES PATENT AND TRADEMARK OFFICE
CERTIFICATE OF CORRECTION

PATENT NO. : 6,074,833
DATED : June 13, 2000
INVENTOR(S) : Weintraub et al.

It is certified that error appears in the above-identified patent and that said Letters Patent is hereby corrected as shown below:

Column 1,
Line 59, replace "by reference MAb's which" with -- by reference, MAb's which -- .

Column 3,
Lines 35-36, replace "e.g. mammals, mice, rabbits, rats, primates etc., with cells expressing OFA" with -- e.g. mammals (mice, rabbits, rats, primates, etc.) with cells expressing OFA --.

Column 4,
Line 2, replace "fiboblastic" with -- fibroblastic --.

Column 5,
Line 29, replace "extracellar matrix" with -- extracellular matrix --.

Column 6,
Line 28, replace "intraperitonealy" with -- intraperitoneally --.

Column 8,
Line 60, replace "injeciton" with -- injection --.

Column 9,
Line 58, replace "15 minuts" with -- 15 minutes --.
Line 64, replace "G.R. Tuross N. termine J.D. 1987," with -- G.R. Tuross N. Termine J.D. 1987, --.

Column 10,
Line 3, replace "minuts" with -- minutes --.
Line 3, replace "incuabation" with -- incubation --.

Column 12,
Line 14, replace "suspenions" with -- suspensions- --.

Column 13,
Line 36, replace "thyomcytes" with -- thymocytes --.
Lines 63-64, replace "cell lines which each represents a different stage" with -- cell lines, each representing a different stage --.

UNITED STATES PATENT AND TRADEMARK OFFICE
CERTIFICATE OF CORRECTION

PATENT NO.    : 6,074,833
DATED         : June 13, 2000
INVENTOR(S)   : Weintraub et al.

It is certified that error appears in the above-identified patent and that said Letters Patent is hereby corrected as shown below:

Column 14,
Lines 1-2, replace "except for in primary" with -- except in primary --.
Line 35, replace "(by western blotting)" with -- (by Western blotting) --.
Lines 60-61, replace "by a western blotting analysis" with -- by a Western blotting analysis --.

Signed and Sealed this

Twentieth Day of November, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.   : 6,074,833
DATED        : June 13, 2000
INVENTOR(S)  : Weintraub et al.

It is certified that error appears in the above-identified patent and that said Letters Patent is hereby corrected as shown below:

Column 4,
Line 48, replace "in vitio" with -- in vitro --.

Column 5,
Line 24, replace "osteogeenic" with -- osteogenic --.

Column 6,
Lines 21-22, replace "'effective atnioitnt'" with -- "effective amount" --.
Line 25, replace "OFA arc administered" with -- OFA are administered --.

Column 8,
Line 29, replace "Wcintraub" with -- Weintraub --.
Line 45, replace "Wcintraub" with -- Weintraub --.
Line 41, replace "wcckly" with -- weekly --.

Column 9,
Line 21, replace "paraformaldchyde" with -- paraformaldehyde --.
Line 24, replace "peroxidase-conijugated" with -- peroxidase-conjugated --.

Column 10,
Lines 12-13, replace "clectroblotting" with -- electroblotting --.
Line 25, replace "lattcr" with -- latter --.
Line 31, replace "mcthionine-free medium" with -- methionine-free medium --.

Column 12,
Line 13, replace "sillgic cell" with -- single cell --.

UNITED STATES PATENT AND TRADEMARK OFFICE
CERTIFICATE OF CORRECTION

PATENT NO. : 6,074,833
DATED : June 13, 2000
INVENTOR(S) : Weintraub et al.

It is certified that error appears in the above-identified patent and that said Letters Patent is hereby corrected as shown below:

Column 14,
Line 62, replace "MAb clid not bind" with -- MAb could not bind --.

Column 16,
Line 4, replace "mlecular" with -- molecular --.

Signed and Sealed this

Eighth Day of January, 2002

Attest:

JAMES E. ROGAN
Attesting Officer
Director of the United States Patent and Trademark Office